United States Patent [19]

Wyeth et al.

[11] Patent Number: 4,951,287
[45] Date of Patent: Aug. 21, 1990

[54] ATOMIC VAPOR LASER ISOTOPE SEPARATION PROCESS

[76] Inventors: Richard W. Wyeth, 887 Northwood Commons, Livermore, Calif. 94550; Jeffrey A. Paisner, 12 Silverlake Dr., San Ramon, Calif. 94593; Thomas Story, 112 Klengel St., Antioch, Calif. 94509

[21] Appl. No.: 206,997

[22] Filed: Jun. 15, 1988

Related U.S. Application Data

[62] Division of Ser. No. 911,842, Sep. 26, 1986, Pat. No. 4,817,101.

[51] Int. Cl.$^5$ ............................................... H01S 3/13
[52] U.S. Cl. ...................................... 372/32; 356/349
[58] Field of Search ................... 372/32, 20; 356/345, 356/346, 349, 350

[56] References Cited

U.S. PATENT DOCUMENTS

| | | | |
|---|---|---|---|
| 3,231,741 | 1/1966 | Siegman | 455/619 |
| 3,350,654 | 10/1967 | Snitzer | 372/55 |
| 3,437,955 | 4/1969 | Enloe et al. | 372/32 |
| 3,547,524 | 12/1970 | Javan et al. | 356/346 |
| 3,856,406 | 12/1974 | Noble et al. | 356/106 S |
| 3,950,100 | 4/1976 | Keene et al. | 356/28 |
| 4,096,448 | 6/1978 | Hayes | 372/18 |
| 4,163,954 | 8/1979 | Hayes | 332/7.51 |
| 4,325,635 | 4/1982 | Sattler et al. | 356/349 |
| 4,385,386 | 5/1983 | Ozeki et al. | 372/20 |
| 4,417,813 | 11/1983 | Bartholomew | 56/349 |
| 4,468,773 | 8/1984 | Seaton | 372/32 |
| 4,552,457 | 11/1985 | Giallorenzi et al. | 356/349 |
| 4,632,554 | 12/1986 | Pearce | 36/349 |

FOREIGN PATENT DOCUMENTS

| | | |
|---|---|---|
| 8704572 | 7/1987 | PCT Int'l Appl. |
| 2164221 | 3/1986 | United Kingdom |

OTHER PUBLICATIONS

Hänsch et al; "High Resolution . . . Tunable Dye Laser"; Physical Review Letters; vol. 27, No. 11; 09/13/1971; pp 707–710.

Jennings et al; "Direct Frequency . . . Thz (633–nm) Laser"; Optics Letters; vol. 8, No. 3; pp 136–138.

Pollock et al; "Direct Frequency . . THz (1.15 $\mu$m) in Neon"; Optics Letters, vol. 8, No. 3; 03/1983; pp. 133–135.

Hlousek et al; "High Accuracy . . . Molecular Iodine"; Optics Letters, vol. 8, No. 6; 06/1983; pp 322–323.

R. L. Barger and J. L. Hall, *Physical Review Letters,* vol. 22, No. 1, Jan. 6, 1969, "Pressure Shift and Broadening of Methane Line at 3.39 $\mu$m Studied by Laser-Saturated Molecular Absorption", pp. 4–8.

J. C. Bergquist, H. U. Daniel, *Optics Communications,* vol. 48, No. 5, Jan. 1, 1984, "Wideband Frequency-Offset-Locked Dye Laser Spectrometer Using a Schottky Barrier Mixer", pp. 327–333.

A. Chu, H. R. Fetterman, D. D. Peck and P. E. Tannewald, *IEEE 1982 Microwave and Millimeter-Wave, Monolithic Circuits Symposium Digest of Papers,* "Heterodyne Experiments from Millimeter Wave to Optical Frequencies Using GaAs MESFETS Above $f_t$"pp. 26–27, Feb. 1982.

J. E. M. Goldsmith, E. W. Weber, F. V. Kowalski and A. L. Schalow, *Applied Optics,* vol. 18, No. 23, Jun. 15, 1979, "Precision Interferometer Calibration Technique for Wavelength Measurements: Iodine Wavelengths at 633 nm, and H$\alpha$", pp. 1983–1987.

*Primary Examiner*—Frnk Gonzalez

[57] ABSTRACT

A laser spectroscopy system is utilized in an atomic vapor laser isotope separation process. The system determines spectral components of an atomic vapor utilizing a laser heterodyne technique.

1 Claim, 17 Drawing Sheets

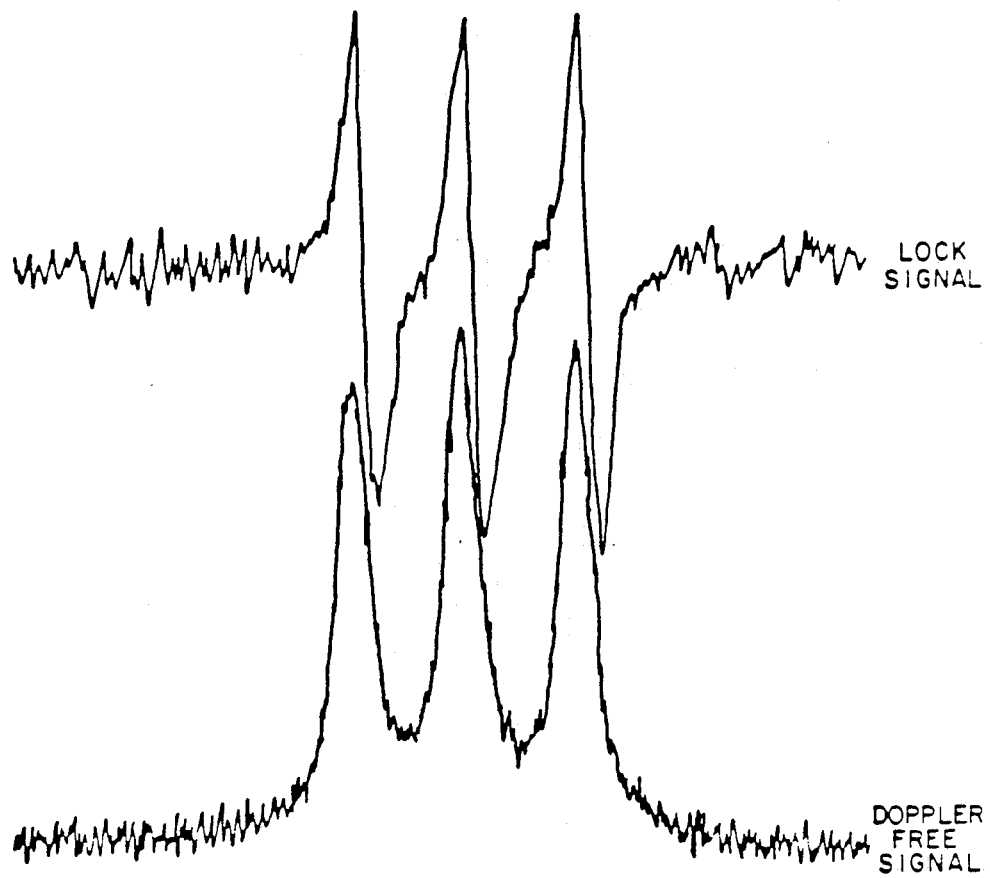
FIG.—3B
LOCK-IN AMPLIFIER CONTROL SETTINGS
FOR IODINE REFERENCE LASER LOCK LOOP
| | LOCK-IN #1 | LOCK-IN #2 |
|---|---|---|
| INPUT SIGNAL | PROBE ABSORPTION SIGNAL | LOCK-IN #1 OUTPUT |
| REFERENCE FREQUENCY | PUMP CHOP FREQ (~2 KHz) | A/O MODUL FREQ (~100 Hz) |
| SENSITIVITY | 1-10 mv | 1-10 mv |
| Q | 100 | 50 |
| TIME CONSTANT | 3 msec | 3 sec |
FIG.—3C

THE LOG FILE MENU (C)REATE  (M)ENU  (R)ETRIEVE  (S)AVE LOG FILE

LOG FILE MENU

RUN TITLE: TEST 1
TIME:  11:47:24  DATE: 01-07-1986
ELEMENT: 12  LINE: 15798
WL1: 6300   WL2: 6200   WL3: 5800
12 REFERENCE LINE: 15800
IODINE A/O SHIFT (MHz): 120
FIELD PLATE VOLTS: 1500
CHANNELTRON: 2700 VOLTS  50 OHMS
ION SIGNAL AMP GAIN:: X5
BOXCAR SETTINGS: DC
MODE:  SYNCHRONOUS
OVEN TEMPERATURE: 1150
LAB:    SPEC
COUNTERS: RS = 4   HR = 3   SA = 1

COMMENTS:

THE MAIN MENU (E)XIT

MAIN MENU

SELECT:

1). LOG FILE MENU.
2). ROUGH SCAN MENU.
3). HIGH RESOLUTION SCAN MENU.
4). SPECTRUM ANALYZER.
5). DISC DIRECTORY (B:).
6). RESET INSTRUMENTS
7). TIMING.

FIG.—5

THE ROUGH SCAN MENU (C)REATE   (D)ISPLAY DATA   (G)O   (M)ENU   (R)ETRIEVE   (S)AVE

ROUGH SCAN MENU

RUN TITLE: TEST 1
ROUGH SCAN FILE:
TIME: 10:50:24  DATE: 12-05-1985
START FREQUENCY (GHz): 13.2
STOP FREQUENCY (GHz): 11.2
NUMBER OF DATA POINTS: 500
NUMBER OF AVERAGES: 5
DISCRIMINATOR VOLTS: 0.6
Y-AXIS VOLTAGE: 2
COUNTER: 3
NUMBER OF MARKERS: 15

COMMENTS:

FIG.—6

THE HIGH RESOLUTION SCAN MENU (C)REATE   (D)ISPLAY DATA   (G)O   (M)ENU   (N)EW MKR.   (R)ETRIEVE   (S)AVE

HIGH RESOLUTION SCAN MENU

```
RUN TITLE:  TEST 1
HIGH RESOLUTION FILE: B: TEST 11.HRS
ROUGH SCAN FILE:
TIME:  10:17:52   DATE: 01-06-1986
WINDOW SIZE (MHz): 50
OFFSET FROM ROUGH SCAN (MHz): 0
NUMBER OF MARKERS FROM ROUGH SCAN: 2
MARKER # TO SCAN: 2
MARKER CENTER FREQUENCY: 11440 MHz
NUMBER OF DATA POINTS: 50
NUMBER OF AVERAGES: 2
NUMBER OF INTEGRATIONS: 0
Y-AXIS VOLTAGE: 4
COUNTER: 3
```

COMMENTS:

FIG.—8

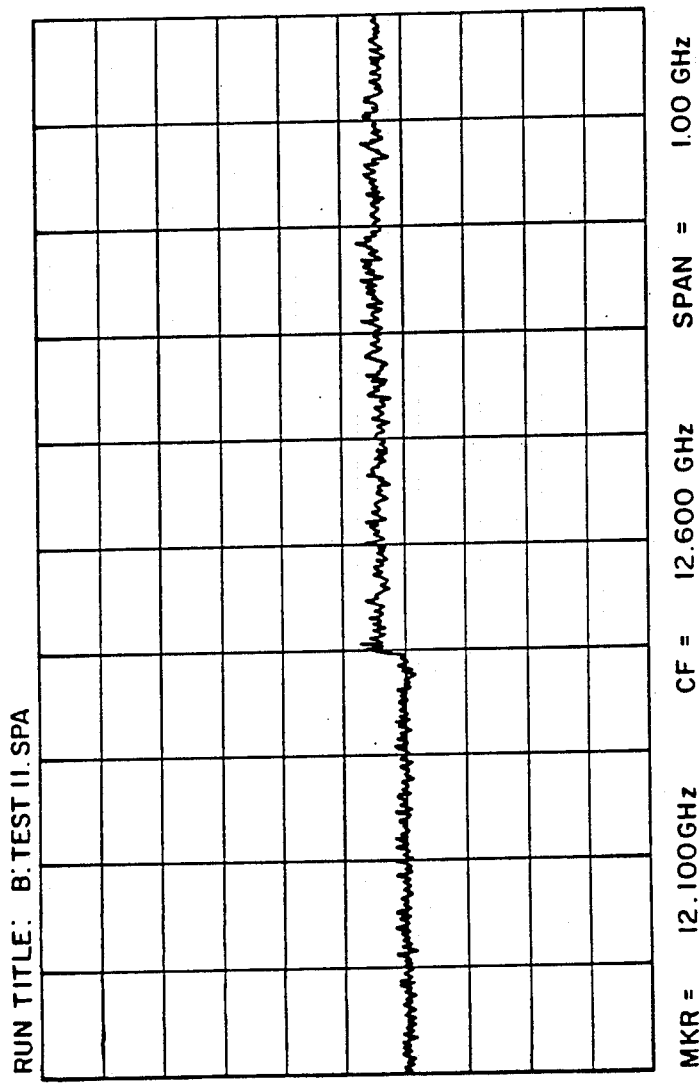
FIG. —10

TABLE 1  SYSTEM SPECIFICATIONS AND LIMITS

| | |
|---|---|
| ACCURACY OF DIFFERENCE FREQUENCY BETWEEN DYE LASERS | 100 KHz MAXIMUM ERROR |
| ACCURACY OF IODINE FREQUENCY LOCK ELECTRONICS | 500 KHz MAXIMUM ERROR |
| ABSOLUTE FREQUENCY ACCURACY OF SCANNED DYE LASER | 1 MHz MAXIMUM ERROR |
| MINIMUM LASER DIFFERENCE FREQUENCY | 100 MHz |
| MAXIMUM LASER DIFFERENCE FREQUENCY | 20 GHz |
| SCAN LASER FREQUENCY RELATION TO REFERENCE ($f_{SCAN} > f_{REFERENCE}$ or $f_{SCAN} < f_{REFERENCE}$) | HARDWARE SELECTABLE |
| DIRECTION OF DIFFERENCE FREQUENCY SCAN (INCREASING OR DECREASING FREQUENCY) | MENU SELECTABLE |

LASER WAVELENGTH RANGE
   DYE TUNING RANGE                  SEE DYE LASER MANUAL
   IODINE REFERENCE RANGE *         500 - 900 nm
   FIBER-OPTICS RANGE **       APPROX 500 - 700 nm
   DETECTOR RANGE              APPROX 300 - 900 nm

* OTHER REFERENCE MATERIALS ARE AVAILABLE WITH DIFFERENT RANGES
 **FIBER OPTICS CENTERED AT .85 nm ARE ALSO AVAILABLE; OTHER
   RANGES CAN BE COVERED USING CONVENTIONAL OPTICS TO COMBINE
   LASER SIGNALS ON THE HETERODYNE DETECTOR.

LASER POWER REQUIREMENTS (MEASURED AT REDUNDANT FIBER COUPLER OUTPUT ON FIBEROPTIC HETERODYNE
  RECEIVER FRONT PANEL. POWER REQUIREMENT FOR FULL FREQUENCY RANGE
  OPERATION; i.e., OUT TO 20 GHz. SYSTEM WILL OPERATE WITH REDUCED
  MAXIMUM LASER FREQUENCY LIMIT WITH LESS LASER POWER)

| | |
|---|---|
| PRODUCT OF REFERENCE LASER POWER AND SCAN LASER POWER | $10^{-6}$ WATTS$^2$ |
| MAXIMUM LASER POWER (EACH LASER) | 10 MILLIWATTS |
| FIBER INPUT COUPLER EFFICIENCY | 10% to 35% |
| NUMBER OF DATA POINTS/SCAN | 1 TO 500 |
| SYSTEM BOOT TIME | 2 MINUTES |
| SCAN TIME | M*N * (0.5 + 0.1 * n) SECONDS |

FIG.—11A

M = NUMBER OF SCAN REPETITIONS
N = NUMBER OF FREQUENCY DATA POINTS
n = NUMBER OF VOLTAGE MEASURMENTS AVERAGED / DATA POINT

| | |
|---|---|
| CRT SCREEN DUMP TIME | <2 MINUTES |
| DATA FILE STORAGE TIME | <20 SECONDS |
| PROGRAM MEMORY REQUIREMENTS | |
| INTERPRETER VERSION | 25 KBYTES |
| COMPILED VERSION | 90 KBYTES |
| DATA FILE MEMORY REQUIREMENTS | |
| LOG FILE | 600 BYTES |
| SPEC ANALYZER FILE | 600 BYTES |
| ROUGH SCAN | 300 + 7*N BYTES |
| HIGH RESOLUTION SCAN | 300 + 7*N BYTES |
| FLOPPY DISK STORAGE SPACE | 356 KBYTES |
| INPUT VOLTAGE RANGE | -10.24 to +10.24 VOLTS |
| RESOLUTION/MAXIMUM ERROR OF SAVED DATA | |
| ANALOG DATA | .0001/.005 VOLTS |
| FREQUENCY | 10K/100K HERTZ |

FIG.—11B

TABLE 2

MINIMUM COMPUTER HARDWARE AND SOFTWARE REQUIREMENTS

IBM PC OR XT
2 DISK DRIVES
256K MEMORY
COLOR GRAPHICS BOARD
PRINTER
PC-DOS OPERATING SYSTEM
MICROSOFT BASIC OR IBM BASIC COMPILER
NATIONAL INSTRUMENTS GPIB-PC2(A) INTERFACE CARD AND SOFTWARE
PRINTER SPOOLER (OPTIONAL, DECREASES DELAY TIME DURING GRAPHICS
SCREEN DUMPS)

FIG.—12

TABLE 3

SYSTEM GPIB ADDRESS ASSIGNMENTS

| ITEM | DECIMAL | HEXADECIMAL | MNEMONIC |
|---|---|---|---|
| COUNTER/SOURCE SYNCHRONIZER | 1 | 1 | EIP |
| SCAN BURLEIGH WAVAMETER | 2 | 2 | BURL |
| REFERENCE BURLEIGH WAVEMETER | 4 | 4 | BURR |
| SRS BOXCAR | 11 | B | BXCAR |
| SOLENOID DRIVER | 12 | C | RELAY |
| HP SPECTRUM ANALYZER | 15 | F | SAZ |

FIG.—13

TABLE 4

DIRECTORY OF THE A SYSTEM DISK, WHICH LISTS FILES
REQUIRED TO EXECUTE THE COMPILED VERSION OF ISCAN.

```
VOLUME IN DRIVE A IS ISCAN EW
     DIRECTORY OF A:\

COMMAND    COM      23210    3-07-85    1:43p
ANSI       SYS       1651    3-07-85    1:43p
PRINT      COM       8291    3-07-85    1:43p
GRAPHICS   COM       3111    3-07-85    1:43p
ASTCLOCK   COM       2547    5-22-85   12:30p
CONFIG     SYS         56   12-10-85    2:33p
ISCAN      EXE      91125    1-13-86    3:33p
AUTOEXEC   BAT         40    1-13-86    3:43p
KEY        TXT         21    1-13-86    3:37p
GPIB       COM      10800   12-12-85    9:08a
     10 FILE(S)    176128 BYTES FREE
```

NOTE - TO RUN ISCAN IN INTERPRETER BASIC THE FOLLOWING
ADDITIONAL FILES ARE REQUIRED:
    BASICA.COM    MICROSOFT IBM BASIC INTERPRETER
    BIB.M    NATIONAL INSTRUMENTS GPIB SOFTWARE
    ISCAN.BAS    ISCAN BASIC SOURCE FILE

FIG.—14

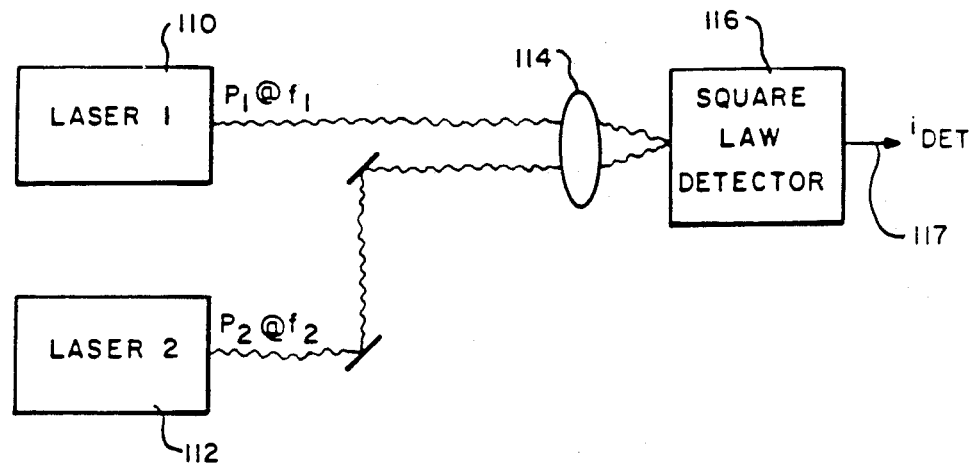
FIG.—15
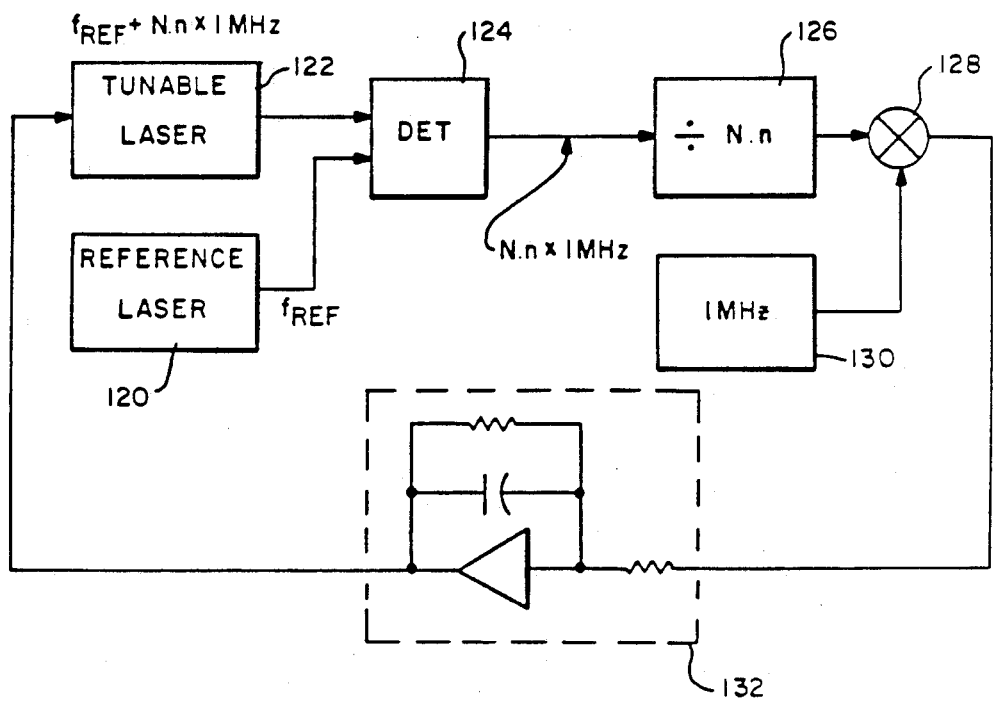
FIG.—16

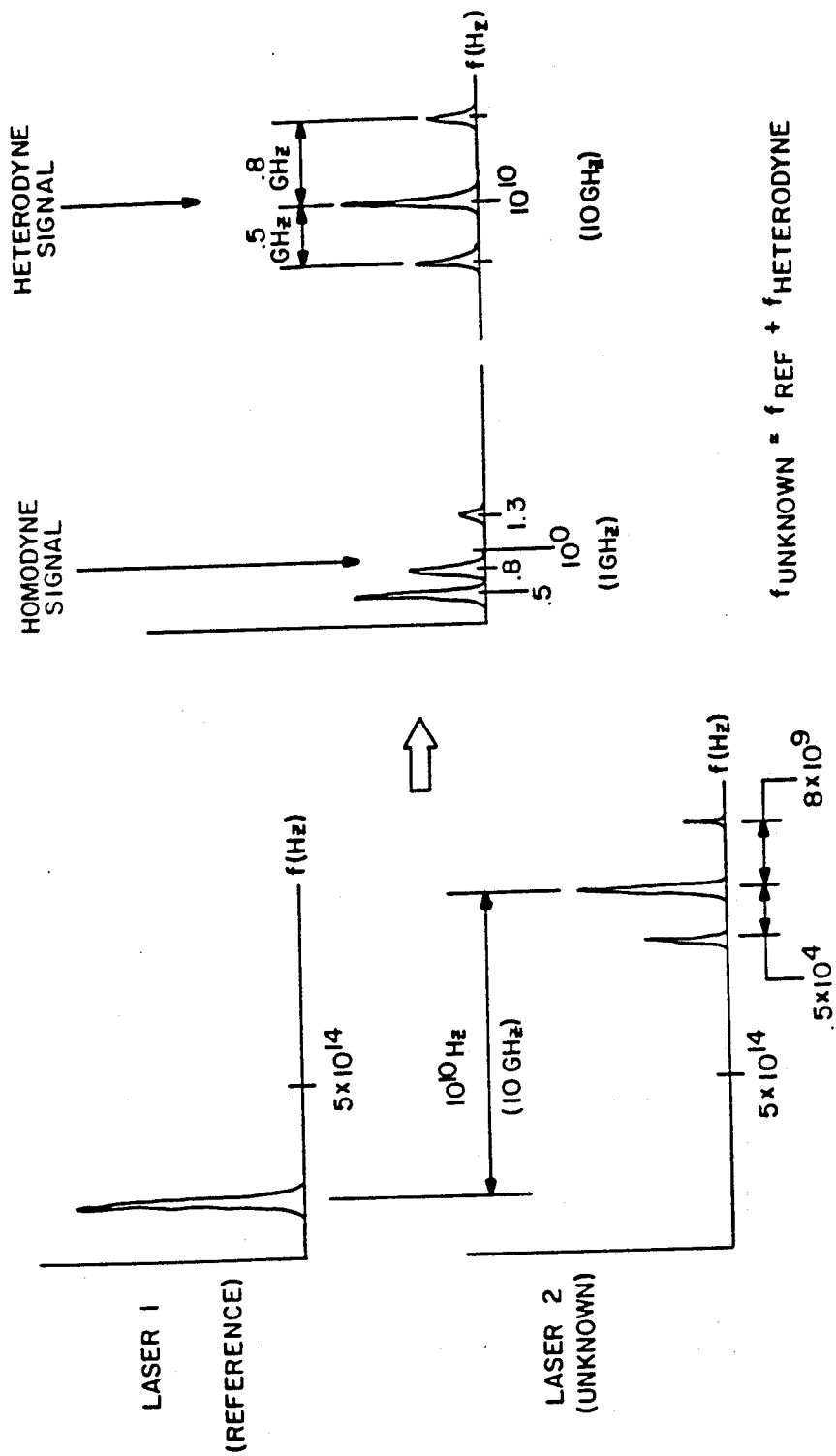

ATOMIC VAPOR LASER ISOTOPE SEPARATION PROCESS

FIELD OF THE INVENTION

The United States Government has rights in this invention pursuant to Contract No. W-7405-ENG-48 between the United States Department of Energy and the University of California for operation under Lawrence Livermore National Laboratory.

This is a division of application Ser. No. 911,842 filed Sept. 26, 1986, now U.S. Pat. No. 4,817,101 which issued on 3-28-89.

BACKGROUND OF THE INVENTION

The present invention relates to a heterodyne laser spectroscopy system. Laser heterodyne control systems are known in the prior art which use phase locked loop techniques to directly phase lock two or more lasers. However, in the prior art, the original phase lock concepts are used to lock lasers to identical frequencies. This approach, however, does not permit the controlled laser's frequency to be set at any value near that of a reference laser and still remain stable or as accurate as the frequency of the reference laser. This limitation is hence not acceptable for purposes of laser isotope separation spectroscopy, atomic vapor diagnostics, processing of precise laser frequency offsets from a reference, and the like.

SUMMARY OF THE INVENTION

It is an object of the present invention to provide an improved heterodyne laser spectroscopy system.

It is another object of the present invention to provide a laser heterodyne system which has application in laser isotope separation spectroscopy systems.

It is another object of the present invention to provide a laser heterodyne system which provides vapor diagnostic applications.

Briefly, the present invention is a laser heterodyning system comprising, in one preferred embodiment, a first tunable laser for generating a laser beam with an adjustable frequency $f_1$ and a second reference laser for generating a laser beam having a reference frequency $f_2$. The system includes detector means for heterodyning the first and second frequencies to form a difference frequency and digital phase locked loop control means responsive to the difference frequency for adjusting the output of the tunable laser to a predetermined frequency output.

Other and additional objects, advantages and novel features of the present invention will be set forth in part in the description which follows, and in part become apparent to those skilled in the art upon examination of the following, or may be learned by practice of the invention. The objects and advantages of the invention may be realized and attained by means of improvements and combinations particularly pointed out in the appended claims.

BRIEF DESCRIPTION OF THE DRAWINGS

The accompanying drawings, which are incorporated in and forming part of the specification, illustrate several preferred embodiments of the invention and, together with the following detailed description, serve to explain the principles of the invention.

FIG. 3B depicts typical iodine hyperfine doppler free and lock signal shapes.

FIG. 3C depicts lock-in amplifier settings for the iodine reference lock loop of FIG. 3A.

FIG. 4 depicts a log file menu.

FIG. 5 depicts a main menu.

FIG. 6 depicts a rough scan menu.

FIG. 8 depicts a high resolution scan menu.

FIG. 10 depicts spectrum analyzer scan graphics.

FIG. 11A and FIG. 11B depict a table illustrating system specifications and limits.

FIG. 12 depicts a table illustration minimum computer hardware and software requirements.

FIG. 13 depicts a table illustrating system GPIB address assignments.

FIG. 14 depicts a table illustrating a directory of the A system disk.

FIG. 15 depicts a block diagram illustrating laser heterodyning techniques.

FIG. 16 depicts a block diagram of a laser heterodyne system according to the present invention.

FIG. 19 depicts a typical heterodyne spectra.

FIG. 20 depicts a typical homodyne spectra.

DETAILED DESCRIPTION OF THE DRAWINGS

System Overview

Figure 1:
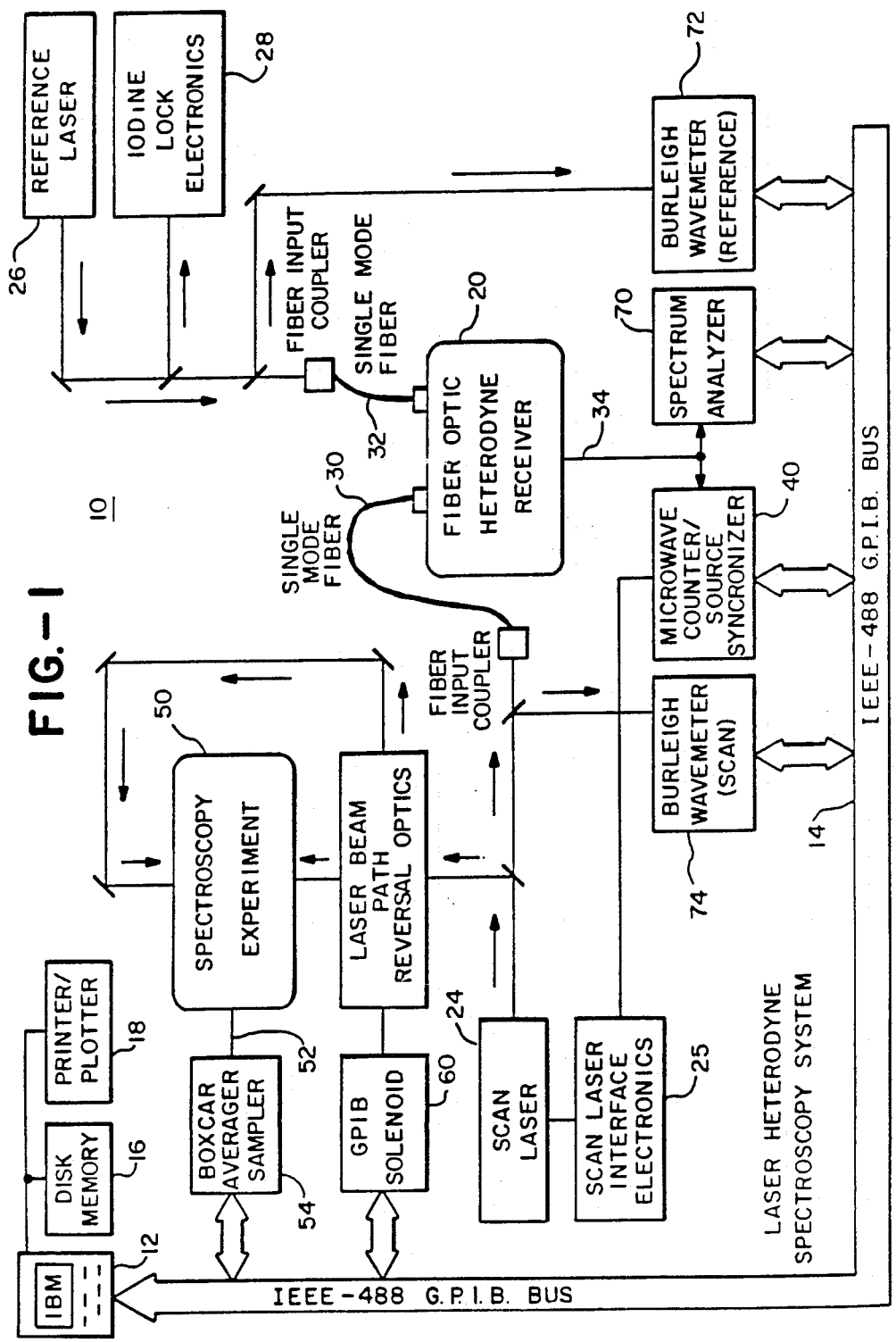
FIG. 1 depicts a block diagram of a heterodyne laser spectroscopy system according to the present invention.

Before describing in detail the various aspects of the present invention, a system overview of a heterodyne laser spectroscopy system will be provided. The Heterodyne Laser Spectroscopy System 10 depicted in FIG. 1 is a system for digitally scanning the frequency of a tunable single mode CW (Continuous Wave) dye laser 26 with high precision while collecting simultaneous data from laser spectroscopy experiments which utilize a scanner laser 24. The system 10 performs heterodyne mixing of the scanned laser frequency with a known stable single frequency reference laser 26 to generate a difference frequency in the microwave range (i.e., 1–20 GHz). Digital phase locked loop techniques are utilized to control the difference frequency by adjusting the frequency of the scanned laser 24. The scanner laser frequency is then known to essentially the accuracy of the reference laser frequency. The reference laser 26 is locked to an accurately known spectral line of molecular iodine, resulting in an overall accuracy in the scanned laser frequency measurement which far exceeds that of conventional techniques.

A block diagram of a heterodyne laser spectroscopy system 10 according to the present invention appears in FIG. 1. The major components of system 10 are interfaced to an IBM personal computer 12 via an IEEE-488

GPIB (General Purpose Interface Bus) 14. A compiled BASIC language program, which is menu driven by an operator, controls the system 10. Several options are available to an operator, such as start and stop frequency, number of data points, number of measurements averaged per datapoint, additional scans with more data averaging, and so on. The data collected from the spectroscopy experiment 50 is immediately displayed in graphical form on the CRT of computer 12 and may be stored for later use along with pertinent identifying data such as title, date, time, iodine reference line frequency, etc., in disk memory 16. Other options allow an operator to print on printer/plotter 18 the graphics generated by system 10, automatically identify the frequency of the maximas of all peaks in the data above an operator selected level, automatically perform high resolution scans on peaks identified in coarse resolution scans, etc. System 10 utilizes data from a conventional optical wavemeter 72 (which has considerably less accuracy), and a sophisticated digitally controlled microwave spectrum analyzer 70 for backup to the operator on the operational status of system 10. Data from these redundant sources can be stored for later use upon menu command from the controller program of computer 12.

The difference frequency $(f_1 - f_2)$ between the scanned laser 24 and the reference laser 26 is generated in the Fiber Optical Heterodyne Receiver 20. This unit 20 interfaces to the two dye lasers 24, 26 over single-mode, fiber optic cables 30, 32, respectively, and supplies a microwave difference signal on lead 34 directly to a commercially available unit called a Microwave Source Synchronizer 40. Source Synchronizer 40 contains a microwave frequency counter, a GPIB controlled programmable frequency divider, phase detector, and servo amplifier portions of a digital phase locked frequency control loop. The output of the servo amplifiers is sent to a unit which properly conditions these signals for the frequency control circuits of the scanned laser 24. The output signal 52 of the experiment 50 is collected by a commercial boxcar system 54 which digitally samples the analog signal at the appropriate time interval for transfer to the computer 12 via the GPIB 14. An additional feature of the system 10 generates solenoid activation signals via circuit 60 for reversing the direction of the laser beam through the experiment 50 while repetitively scanning the laser frequency and replotting the spectroscopy data. This procedure enables an experimenter to detect and correct for Doppler shifts in the spectroscopy data due to misalignment of atomic beams or other sources of the spectroscopic species under study.

Figure 7:
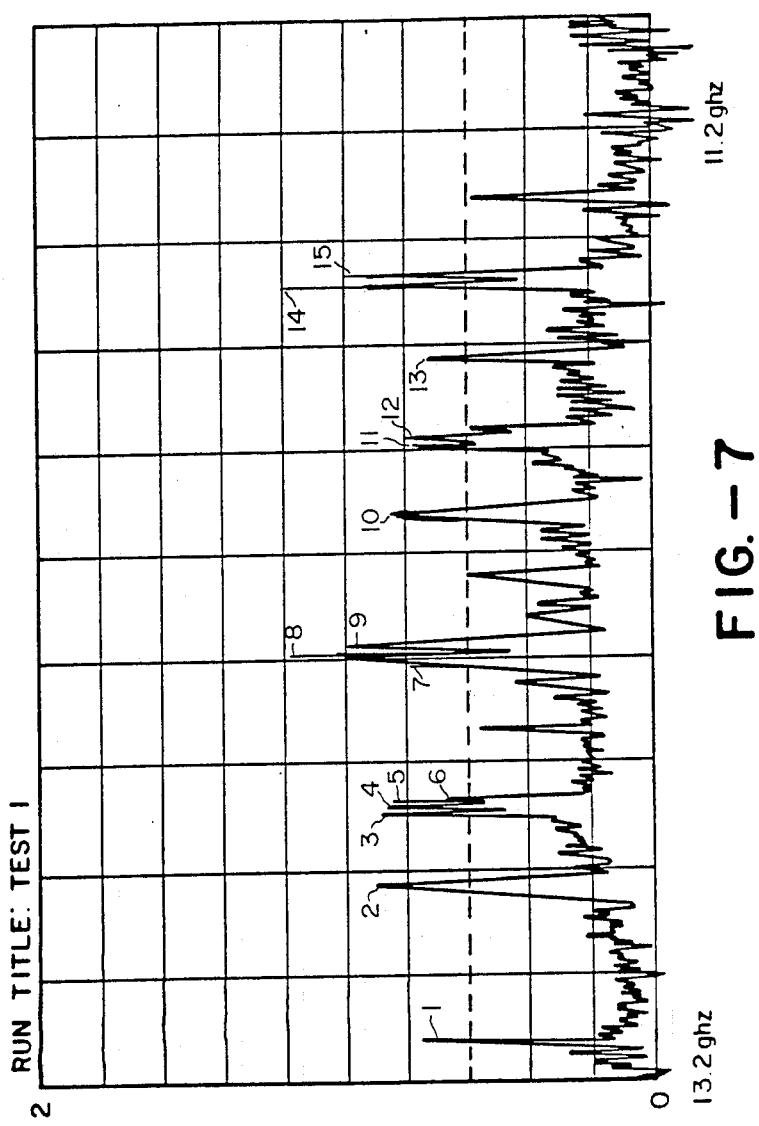
FIG. 7 depicts rough scan graphics.

A CRT screen dump of the PC graphics generated by system 10 in the rough scan or low resolution mode is shown in FIG. 7. This plot was generated from a Doppler free molecular iodine experiment. The data actually contains hyperfine structure from the two iodine absorption lines which are by chance approximately coincident in the spectrum. The discriminator feature has been used to identify all 15 peaks in the data which exceed the preset level of 0.6 volts. The total scan width is 2 GHz and 5 readings of the output signal were averaged at each of 500 data points to generate the data set. A screen dump of the operator's menu selections for this scan is shown in FIG. 6. The time required to make this scan was approximately 500 seconds.

All data files created by the system utilize standard ASCII characters for representation of all quantities and are in absolute units to avoid confusion. Labeling and format characters are used so the files print in readable form to avoid losing data in the future by losing the "decoding" information. Additional user programs allow retrieval, graphical display, data analysis or processing, as well as generation of hard copy listings and plots from archived data files.

Specifications

The important specifications of the heterodyne laser spectroscopy system 10 are summarized in FIG. 11. More detail on several of these specifications follows or may be found in the Theory of Operation section.

A. Accuracy of Frequency Measurement

The laser difference frequency is very accurately controlled by a digital phase locked technique and its long term average error is insignificant. The quoted maximum error specification of 100 KHz arises from phase noise in the frequency loop and the comparatively short lock time between data sample points. This can be optimized if required, but has been traded off for faster scan time.

The absolute frequency error of our measurements is limited mostly by the available data on the iodine hyperfine reference line frequencies. It is estimated that lines can be absolutely calibrated throughout the portion of the optical spectrum of interest to well characterized lines with sufficient accuracy to achieve an overall maximum absolute frequency error of 1 MHz.

B. Laser Wavelength

At least four independent factors define the useable laser wavelength range of system 10; the dye and optics installed in the tuneable dye lasers, the availability of spectral reference lines for reference laser locking, and the spectral range of the fiber optics and the optical detector in the fiber optic heterodyne receiver 34.

Dye Laser Tuning Range—The manuals for the individual dye lasers (which are commercially available) should be consulted. In general, dyes and optics are available to support most CW dye laser systems which cover overlapping portions of the green through red visible and the near IR spectrum. The blue and ultraviolet end of the spectrum is difficult to reach with CW dye laser systems, but may be reached by second or third harmonic generation of the output from CW laser oscillator/pulsed dye amplifier systems. The pulse amplifier is required to achieve the high peak powers necessary for harmonic generation in crystals with non-linear optical properties. The harmonic generator's pulsed laser output frequency is an exact integer multiple of the input CW dye laser oscillator, which may be controlled by the heterodyne laser spectroscopy system 10.

Special Reference Lines—Molecular iodine lines are available at somewhat random intervals which rarely exceed 10 GHz to 20 GHz at the wavelengths of interest from approximately 500–900 nanometers. Approximately 20 of these lines have been well characterized and may be used as standards for calibrating additional lines by a series of jumps through the spectrum using intermediate lines. It is hoped to be able to generate an extended catalog of acceptable reference lines by using the heterodyne laser spectroscopy system 10 of FIG. 1 with two Doppler free iodine spectroscopy subsystems (one on each laser). At infrared wavelengths alternate spectroscopic standard materials are available.

Fiber Optics Wavelength Range—Single mode fiber optics must be operated close to their design optical wavelength for minimum attenuation or degradation of mode quality. As the wavelength becomes too long, the attenuation will rapidly increase. As the wavelength becomes too short, additional transverse modes will begin to propagate in the fiber which will reduce the heterodyne difference signal strength at the detector. The single mode fiber used in the system is designed for operation at the HeNe laser wavelength of 633 nanometers. It will function with reduced signal strength over a range of from approximately 450 to 700 nanometers. Single mode fiber optics centered at 850 namometers are also commercially available.

Detector Wavelength Range—Gallium Arsenide has a band-gap energy corresponding to a wavelength of approximately 900 nanometers and has no response at longer wavelengths. The responsivity at photon energies above the bandgap energy is very high, and therefore is high throughout the visible range.

C. Laser Power Requirements

Laser power requirements are dependent on many factors, including laser wavelength, fiberoptics and detector utilized, minimum and maximum laser difference frequency, amplifiers utilized, and other factors. More complete data on this specification than appears in FIG. 11 will require a detailed analysis of the specific intended application of the system. The specifications given generally apply to the use of the appropriate fiber optics, a Gallium Arsenide FET detector, 25 db of microwave amplification following the detector for signals above 8 GHz, and operation in the yellow through red end of the visible spectrum.

D. Software and Computer System Specifications

System software and computer requirements and specifications are further clarified in the corresponding portions of Operating Instructions and Theory of Operation.

Operating Instructions

A. Introduction

The operating instructions concentrate on the operation of the heterodyne laser spectroscopy system computer controller program. For purposes of discussion, it is assumed that an operator is familiar with the detailed operating and optical alignment procedures for dye lasers 24, 26, the microwave source synchronizer 40, and other peripheral equipment of FIG. 1. Instructions for operating this equipment are given in the manufacturer's literature.

B. System Turn-on and Initialization

The first step in operating the system is to apply power to all of the system instrumentation and to bring the lasers up to their normal operating conditions. Next, lock the reference laser 26 to the proper iodine line and set the scan laser frequency to roughly the starting scan frequency. The difference frequency should be observable on the microwave counter 40 and on the spectrum analyzer 70. It should also be possible to phase lock the difference frequency to the start frequency using the manual controls on the EIP source synchronizer 40.

The EIP unit 40 has internal microprocessor program routines which automatically test for and calculate the appropriate servo gains for the frequency control feedback signals. However, these routines are only exercised by instructing the unit to change the laser offset frequency. Before proceeding with the operation of the system computer program, it is usually expedient to use the EIP unit's manual controls to change laser offset frequency through successively larger and larger increments until it will successfully change the offset frequency from the start scan frequency to the stop scan frequency without losing lock. This allows the EIP Model 578 to "learn" the proper gain factors, and also insures that the scan laser can be scanned over the whole planned interval without a mode hop.

C. Running the ISCAN Program

The system is now ready for running of the ISCAN program. After turning the IBM PC 12 on, allow approximately two minutes for booting of the PCDOS operating system and running of the specialized heterodyne laser spectroscopy system initialization command files. The following prompt will appear on the computer's CRT when the system has been initialized, "AJ". Pushing the "F10" key in response to the prompt runs the compiled version of the ISCAN program.

D. The Log File

The ISCAN program begins by displaying the log file menu which typically appears as shown in FIG. 4 of the CRT. Pressing "C" allows creation of a new menu in response to the illustrated CRT system parameter prompts, pressing "R" and responding to the CRT prompt with a stored file name retrieves an old log data file and displays the completed menu, pressing "S" saves the displayed log file menu, and pressing "M" initiates display of the main menu.

The program enters the log file menu at start up to remind the operator that a log file must be either created or retrieved if data is to be taken. The log file is an ASCII text file only (no data), containing information pertinent to the general experiment and is not used as input data for control of the scans. Therefore, information can be entered or omitted at the discretion of the experimenter. The only exception to the preceding statements is the boxcar "Mode:" log file menu entry. This entry controls the operating mode of the boxcar which samples the spectroscopy experiments data. The experimenter can respond with either "Asynchronous," with the boxcar sampling occurring immediately after command from the ISCAN program, or "Synchronous," with boxcar sampling occurring on the next external trigger signal after a command from ISCAN. This information is saved on disk in the log file and used to reinitialize the boxcar if an old log file is retrieved. An example of the use of synchronous data collection is to trigger the boxcar sample gate to be coincident with a pulsed laser pulse used for a lower level step of a multiple level photon absorption spectroscopy experiment.

As data files are generated and saved by the experimenter, they are automatically numbered by adding a sequential integer to the run title name for use as a unique file name for the data. The present data file name integer is saved in the log file, so additional data file names are automatically numbered in the proper sequence after retrieval of an old log file. This allows the operator to suspend operation of the experiment, turn off the equipment, conduct other experiments, or return to the original experiment, at any time. After creating or retrieving a log file menu the operator should proceed to the main menu. Log file names are of the form "TITLE.LOG". Log file names may be up to five characters in length. Alpha characters only are suggested to avoid confusion in the numbering of datafiles. Combined datafile names may be up to 8 characters in length allowing a minimum of 999 possible datafiles for each log file.

E. The Main Menu

The main menu is displayed on the CRT, as shown in FIG. 5. The main menu allows the user to return to the log file menu, select one of the three scan and data acquisition routines, rough scan, high resolution scan, and spectrum analyzer, or select one of three auxiliary routines; disk directory, reset instruments, and timing. The operator makes the selection by pressing the appropriate number key, ("1"through "7"). Pressing "E" allows the operator to exit the ISCAN program.

F. The Rough Scan Routine

The rough scan routine is used primarily for wide frequency scans to locate peaks in the data for subsequent scanning in the high resolution mode. The rough scan menu is shown in FIG. 6. The operator types "C" to create a new menu, "R" to retrieve an old data file and menu, D" to display the data associated with the menu (if any exists), "G" for go to start a rough scan, "S" to save the menu and data from a scan, and "M" to return to the main menu. "Number of averages" means number of analog to digital conversions of the boxcar output voltage per frequency data point. The data plotted and stored is the average of these readings. "Discriminator Volts" sets the voltage level for the peak detector. "Y-Axis Voltage" sets the maximum number on the Y axis of the data plot. "Counter" indicates the data file name integer which will be used if data is saved, and "Number of Markers" indicates how many peaks were found in the data which exceeded the discriminator level.

The graphics generated by a rough scan plot on the CRT are shown in FIG. 7. Note that the peak frequencies are all listed and sequentially numbered. The discriminator voltage level is shown as a dotted line. The run title, date and time are also provided. Data collection can be suspended during a scan by pressing the "E" key. The system remains in the graphics mode and data collected up to this point is still available for display, hard copy or saving to a disk data file. After normal or operator induced termination of a scan, several other options are available, as indicated on the top of the graphics display. Pressing "H" allows entering the high resolution scan routine which uses peak marker data collected during the rough scan, pressing "L" lists the markers, pressing "R" for redo repeats the scan, pressing "S" saves the data in a rough scan data file and increments the data file name integer, and pressing "M" causes a return to the rough scan menu.

Rough scan data files are ASCII files and will print out in tabular form in real decimal units, complete with titles. They contain the rough scan menu and two data arrays; the actual scan data consisting of frequency, boxcar voltage, Burleigh wavemeter readings, and Fabry-Perot interferometer detector voltage readings, as well as the peak marker data consisting of marker number and the corresponding peak frequency. Rough scan data file names consist of the run title followed by the appropriate data file name sequential integer and the extension ".RFS".

G. The High Resolution Scan Routine

Figure 9:
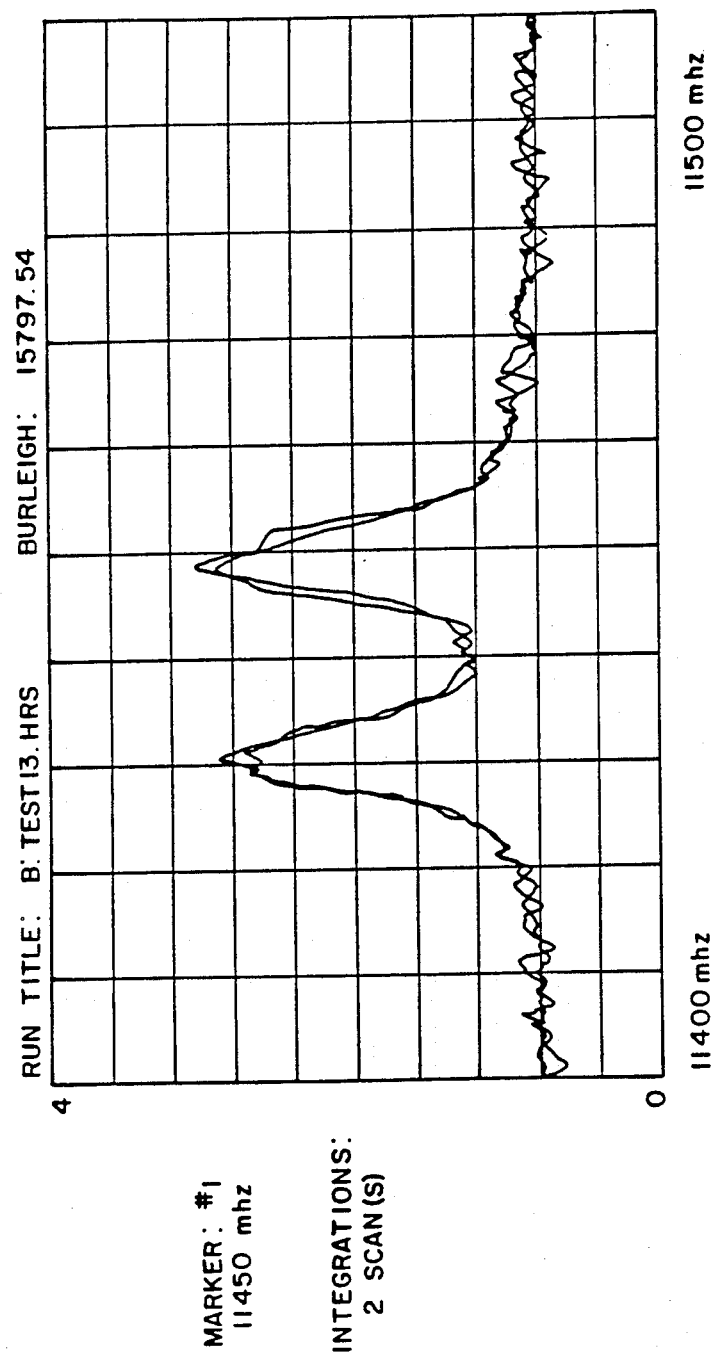
FIG. 9 depicts high resolution scan graphics.

The menu and graphics generated by the high resolution scan routine are shown in FIG. 8 and FIG. 9, respectively. There are three basic differences between the high resolution scan and the rough scan.

In the rough scan routine, the menu specifies the "Start Frequency (GHz): and the "Stop Frequency (GHz)" of the scan. However, in the high resolution routine, the operator selects a frequency "Window Size (MHz)" for the scan. The scan is centered about a peak frequency provided from previously stored rough scan data. The operator only needs to specify the "Marker # to Scan" and the "Marker Center Frequency" will display the corresponding value obtained from the ".RFS" rough scan data file. The operator has the option of arbitrarily controlling the center of the scan window by choosing a marker number integer which is one greater than the "Number of Markers from Rough Scan." ISCAN will then query the operator to select the marker center frequency.

The second difference between the scan routines is the provision in the high resolution scan routine for correcting Doppler shifted absorption spectroscopy data caused by source misalignment. The routine automatically provides a solenoid activation signal for reversing the laser's propagation direction through the source beam after the initial scan. The scan laser's frequency is rescanned from the previous stop value back to the start value while displaying the data acquired as an additional trace on the graphics plot. Any Doppler shift will now be apparent and measureable since the reversal of the laser's direction will reverse the sign of the Doppler shift. True peak frequencies may be calculated by averaging the frequencies of the two corresponding Doppler shifted peaks. If the Doppler shift in the data is large and the operator wishes to conserve scan time, an offset in the center frequency of the reverse direction scan can be specified in the menu ("Offset from Rough Scan (MHz)).

Finally, the high resolution scan routine has an averaging feature which allows additional bidirectional scans to be performed by pushing the "I" key after a previous scan finishes. The new data will be integrated with the old data to obtain a true average of all previous data. The number of integrations of the data is displayed in the menu and on the graphics plot of the averaged data.

The high resolution scan data files consist of one array of voltages and frequencies (in the order taken). File extension is ".HRS".

H. The Spectrum Analyzer Scan

This routine allows the operator to plot, save, retrieve or display retrieved spectrum analyzer data taken by an HP 8566B Spectrum Analyzer 70 of FIG. 1. This can be done in two modes: "P" for plot (single sweep), and "C" for continuous (continuous sweep). A typical graphics presentation appears in FIG. 10. Data file extension is ".SPA".

I. Auxiliary Main Menu Routines

Data Disk Director displays a directory of the B: disk (data disk). After viewing or printing the directory, the operator may return to the main menu.

Reset Instruments performs a software reconfiguration of the GPIB bus 14 of FIG. 1 and all instruments connected to it for compatibility with ISCAN. A "Selected Device Clear" is not performed.

Timing allows optimization of scan time by adjustment of the unlock and lock wait times for the EIP Source Synchronizer. Conservative default values are configured in the software.

J. Hard Copy Listings of Menus and Data Plots

A hard copy of the IBM PC CRT screen may be obtained at any time by simultaneously pressing the "Shift" and the "PrtSc" keys. Program operation is suspended until the printing operation is completed, which requires approximately two minutes for a graphics screen. Program down time may be reduced by investing in a printer spooler which is a buffer memory device that provides temporary storage of the screen information during the time required for the printer to complete the hard copy.

Theory of Operation

A. Fiber Optical Heterodyne Receiver

The fiber optical heterodyne receiver 20 of FIG. 1 senses the optical output of both the reference laser 26 and the scanned laser 24 to generate the microwave difference frequency signal on lead 34. A block diagram of a fiberoptic interfaced heterodyne receiver appears in FIG. 2. The optical receiver 20 includes front panel fiberoptic input connectors for the fiber optics to the two lasers, a fibercoupler 100 to combine the two laser signals into a single signal (f1–f2), which is in turn delivered to a wideband Gallium Arsenide FET detector 102 via fiber optics, and a wideband microwave amplifier 104 which amplifies the microwave laser difference signal for output to a front panel connector. A DC power supply and microwave response bias tees for FET detector DC biasing, as well as a current meter for monitoring operation of the detector, are also built into the unit. A redundant output from the fiber coupler is provided on a convenient front panel fiber optics connection for use with an external optical power meter 106 to monitor laser input power to the unit.

Figure 2:
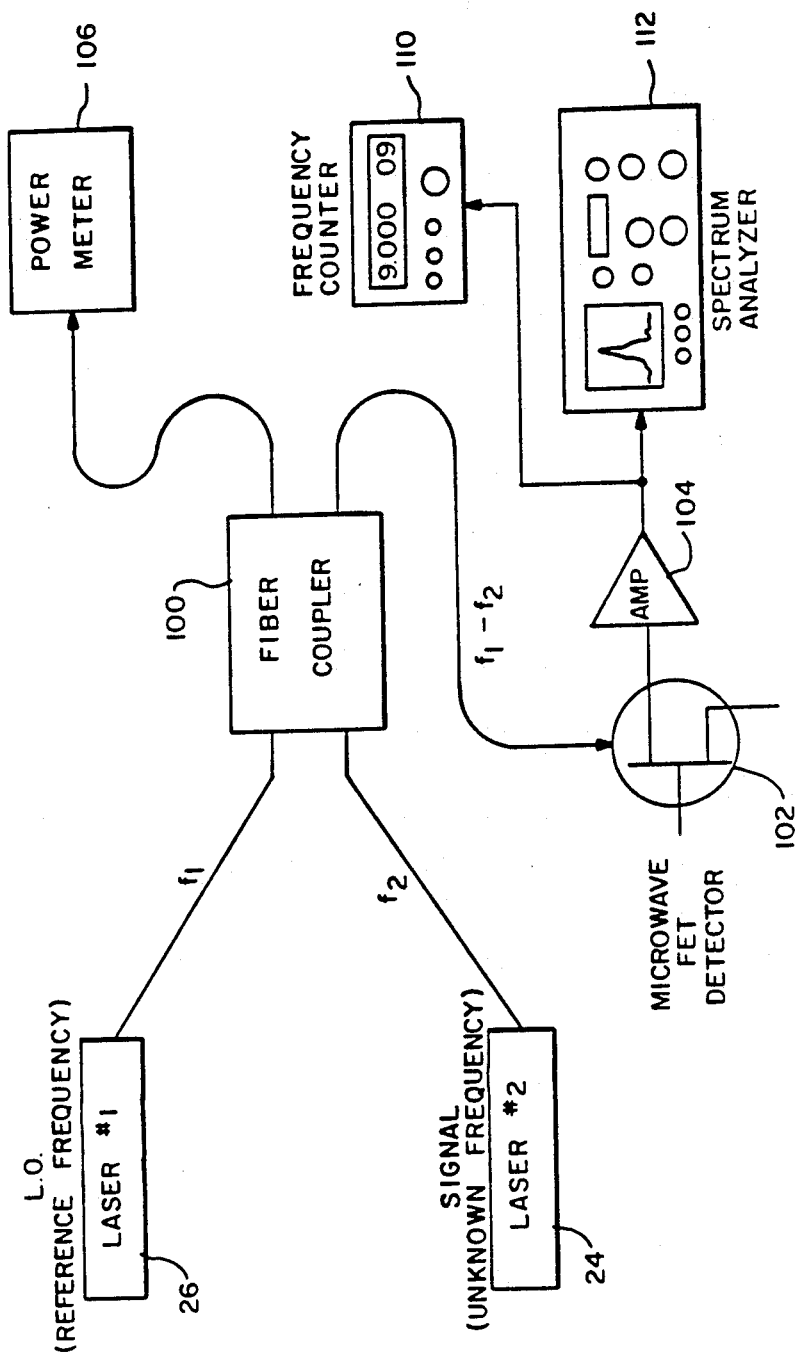
FIG. 2 depicts a block diagram of a fiberoptic heterodyne receiver.

In principle, the unit 20 functions similarly to a heterodyne radio frequency receiver. The reference laser light, corresponding to a local oscillator rf, is mixed with the scanned laser light, corresponding to a signal rf, in a nonlinear device which generates the difference frequency signal. In the rf heterodyne receiver, the nonlinear device is generally a diode or nonlinear product type amplifier which follows the rf signal sensing antenna. The nonlinear device 102 used in the optical receiver 20 of FIG. 2 is a square-law semiconductor optical detector which generates photocurrent in proportion to the intensity of the incident optical signal. The optical detector 102 performs a dual function when compared to the rf receiver. It functions as both the converter of electromagnetic radiation to an electronic signal or antenna, and as the nonlinear difference frequency generating device.

The frequency of light is very high, approximately 500 THz for red light and, therefore, the difference frequency between the reference laser 26 and the scanned laser 24 of FIG. 1 can be a very high frequency. To achieve a practical value for the maximum controllable offset frequency between the two lasers, a very wide bandwidth optical detector is required. For this reason, a microwave Gallium Arsenide MESFET has been used as an optical detector. The detector is custom packaged to interface the most photo-sensitive portion of the FET chip directly to a single-mode optical fiber input. In FIG. 2, a fiber coupler 100 is used to combine the two laser light signals $f_1$, $f_2$ from separate optical fiber inputs. This system greatly simplifies the optical alignment procedure. The optical heterodyne process requires that the optical wavefronts of the two optical inputs be perfectly parallel for maximum conversion efficiency and frequency response. The size and location of the focus of optical input signal on the detector is also critical. The use of the fiber optics and fiber-optical connectors automatically insures maximum performance without tedious alignment procedures. Fiber optics also allow remote location of lasers and rapid interchangeability of lasers, detectors, and so on.

B. Microwave Source Synchronizer

The microwave source synchronizer of FIG. 1 is a commercial unit, EIP Model No. 578. The unit 40 consists of a microwave frequency counter which functions as a programmable frequency divider, and other necessary portions of a digital phase lock frequency control servo such as a reference oscillator, phase detector and servo amplifier. A tunable YIG pre-selector filler precedes the input to the microwave counter. The unit 40 is controllable in several operating modes from the front panel and by external computer via a PIB connection. Internal microprocessor subroutines are programmed with algorithms which aid in the acquisition of the microwave difference frequency signal and the set point and stabilization of the laser difference frequency control servo loop. Details on the theory of operation, operating and programming instructions, and maintenance procedures of this unit are furnished in the manufacturer's operating and service manual.

C. Reference Laser Iodine Locking Subsystem

Figure 3A:
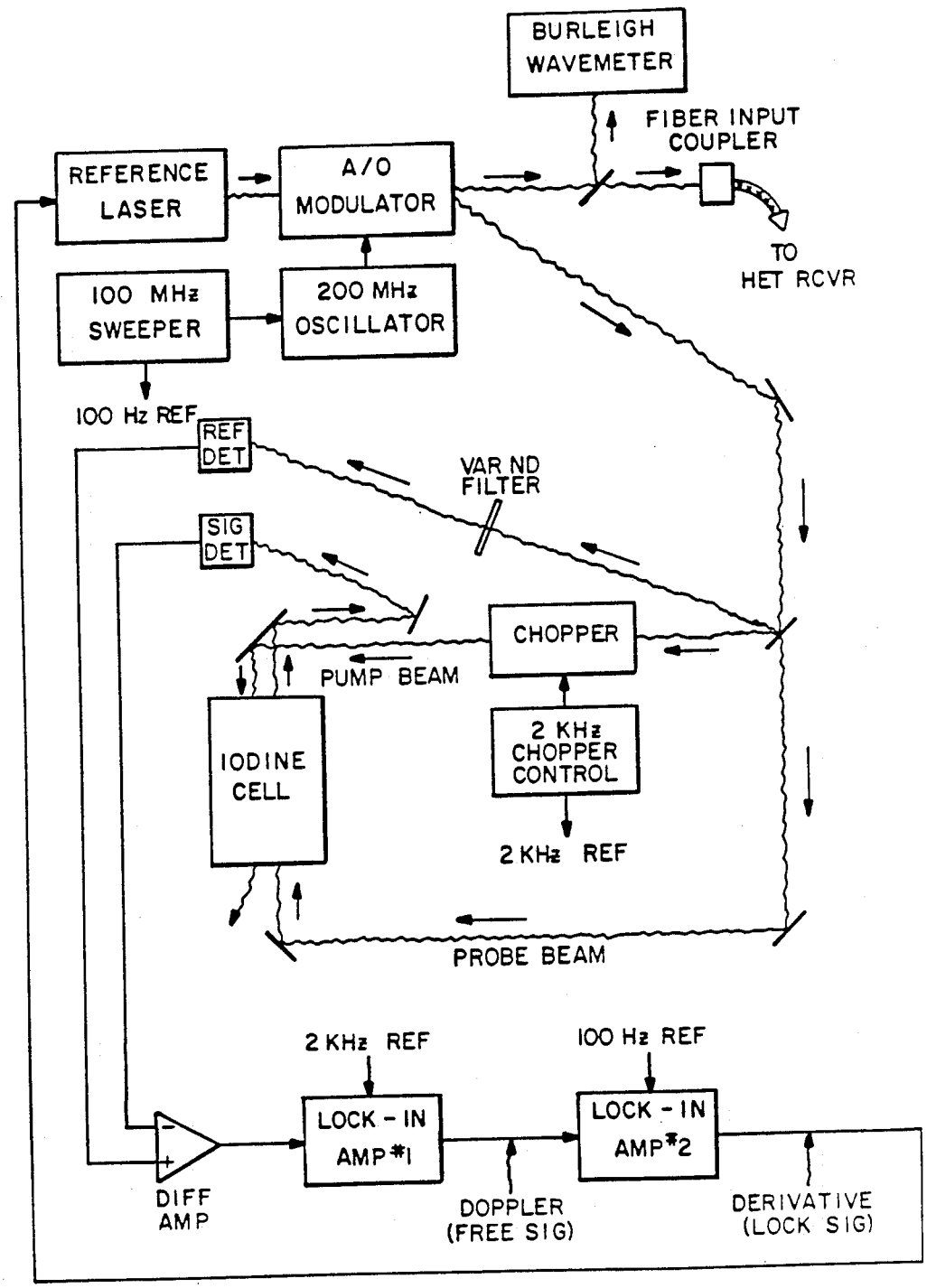
FIG. 3A depicts a block diagram of an iodine reference locking subsystem.

The reference dye laser 26 is locked to a hyperfine absorption line of molecular iodine by the method outlined in FIG. 3A. The hyperfine lines are resolved using Doppler free saturated absorption spectroscopy with counterpropagating pump and probe beams through a cell containing low pressure iodine vapor, as described in the art by Hansch, Shahin and Schalow. The pump beam is mechanically chopped at around 2 KHz. The Doppler free iodine signal appears as intensity variations in the probe laser beam which are lock-in amplifier detected at the pump beam chop frequency.

Both the probe beam and the pump beam are also acousto-optically frequency modulated with a carrier frequency of 200 MHz, a deviation of approximately 500 KHz, and a modulation frequency of approximately 100 Hertz. The derivative of the hyperfine absorption signal with respect to laser frequency then appears at the output of a second cascaded lock-in amplifier which phase sensitive detects at the 100 Hz FM modulation frequency. This laser frequency derivative signal is amplified and low pass filtered for use as the feedback signal to servo control the reference dye laser frequency. Since the acousto-optic modulator is external to the laser cavity, the actual dye laser output is not frequency modulated and is stably locked with respect to the center frequency of the hyperfine iodine absorption line.

The reference laser frequency is offset from the line center frequency by a constant amount due to the Doppler frequency shift introduced by the acoustooptic modulator. This frequency shift is equal to the carrier frequency of the acoustooptic modulator, which is digitally synthesized in a commercial waveform generator and is known to better than 1 Hertz. Therefore, the reference laser's absolute frequency is easily calculated by adding this known offset to the iodine hyperfine line frequency. FIG. 3B shows a typical plot of the output of the raw Doppler-free absorption signal output from the first lock-in amplifier, and the frequency derivative signal from the second lock-in amplifier output. The Doppler-free absorption signal and its derivative with respect to frequency have been recorded versus time on a strip chart recorder as the laser has been scanned in frequency over several iodine hyperfine lines. The derivative signal has a shape which allows direct use as the feedback signal to frequency servo lock the laser to a selected hyperfine line. Lines are acquired by first disabling the feedback signal, then scanning the laser to the desired Doppler-free signal peak (while observing the expected reversal of polarity of the open loop feedback signal on either side of the peak), and then enabling the feedback signal to achieve lock. The recommended lock-in amplifier control settings for proper operation of the iodine line locking system are indicated in FIG. 3C.

Proper operation of the reference laser lock loop may be verified by monitoring the laser frequency servo signal. During lock, the servo signal is essentially DC and lies in the linear control range of the laser. A reference Burleigh wavemeter 72 as depicted in FIG. 1 provides additional confirmation that the laser 26 is locked and has not mode-hopped or jumped to another iodine line.

D. Scan Laser Interface Electronics

The scan laser interface electronics 25 of FIG. 1 conditions the output signal from the microwave source synchronizer for stable feedback servo control of the frequency of the scan laser 24. The unit 25 contains servo amplifiers with the specific gain and frequency response characteristics required by the tunable dye laser under control.

In general, both the SpectraPhysics and Coherent ring dye lasers routinely utilized by the system 10 require two electrical signals as inputs for frequency control. The first signal is a low frequency response, or DC, signal for control of a galvonometer driven optical element which varies the optical length of the cavity. The galvonometer rotates a glass plate which is positioned at Brewster's angle with respect to the laser beam to reduce reflective losses. Since the Brewster plate has significant mass, this element has insufficient bandwidth to compensate for other unwanted rapid fluctuations in the cavity length such as turbulent flow of the dye jet, mechanical vibrations of optical elements, etc. However, a very wide range of DC adjustment in cavity lengths is achieved, allowing coarse servo control of the laser's frequency. The rapid fluctuations in cavity length are compensated for by moving one of the cavity mirrors with a piezo-electric control crystal. The mirror and its control element are very light, allowing a high frequency response. A second high frequency response, or AC, signal is generated to drive this element. Further conditioning of the exact gain and frequency response of each signal is required for servo loop stability compensation.

The scan laser interface electronics 25 is customized for the particular model of laser utilized. Modifications may also be required for major changes in the configuration of the laser such as dye type, pump source, or cavity optics.

E. Tunable CW Dye Lasers

The heterodyne laser spectroscopy system 10 of FIG. 1 has been successfully used to control the Coherent 699 series of tunable ring dye lasers. However, dye lasers such as a Spectra-Physics ring dye laser could be operated with the system. Standing wave dye laser systems also furnish adequate output power for proper operation of the heterodyne detection portion of the system. The configuration of the scan laser frequency servo loop is also similar, but the exact gain and frequency response compensation of required control signals must be customized to a particular laser.

Operation and maintenance instructions for the tunable dye laser utilized by the system are available from the manufacturer's manuals. It is emphasized that issues of laser safety should be addressed by qualified personnel before installing or operating any laser system.

A future modification of the system may include the ability to select specific iodine reference lines for automatic acquisition locking of the reference laser frequency by computer control. In the current configuration, the operator must manually position the reference laser's frequency close to the reference line and then lock the servo loop. The manual acquisition is achieved using a Burleigh wavemeter 74 for a coarse indicator and by actually scanning the laser over the iodine hyperfine line structure to recognize the specific line within the pattern. The automated control functions of the Coherent 699-29 Automated Ring Dye Laser system appear to be adaptable to this function with minor software modification.

F. Burleigh Wavemeter and Hewlett Packard 8566B Spectrum Analyzer

The Burleigh wavemeter 74 of FIG. 1 provides a coarse indication of laser frequency with a resolution of approximately 300 megahertz. A GPIB interface allows the data acquired by the wavemeter to be directly transferred in digital form to the system controller computer. The system may be configured with dual wavemeters 72, 74 for the reference laser 26 and scan laser 24 or with a computer activated opto-mechanical multiplexer to share the use of one wavemeter. Operation of both lasers 24, 26 may be monitored for a coarse loss of lock indication. Burleigh wavemeter readings are automatically stored in data files along with the high precision data for later verification of proper system operation.

The system software also allows the operator to monitor a Hewlett Packard Model Number 8566B spectrum analyzer 70 which displays the spectrum of the laser heterodyne difference signal and periodically store this trace data for future reference. Stable operation of the laser offset frequency control loop is best verified through use of the spectrum analyzer.

G. GPIB Controller Computer System

An IBM PC 12 has been utilized as the system controller since it is widely available and well supported in all areas including available software, hardware options and maintainability. Since all of the commercial test equipment used in the system have GPIB interfaces, the system components communicate over a GPIB bus 14. The PC 12 is configured with a National Instruments Model No. GPIBPC2(A) interface board. The controller program has been written in IBM Microsoft Basic. The program may be run using compiled Basic (for normal operation), or interpreter Basic (for testing of custom modifications). The program will execute much faster in compiled Basic, but since the program is quite lengthy, compilation time is long (approximately ten minutes). Compile time drastically increases the turnaround time between tests of iterations of softward design changes. If extensive modifications are anticipated, the use of the Microsoft Basic interpreter should be considered. The minimum computer hardware and software requirements are listed in FIG. 12.

The use of fiber-optics for optical connections to the reference and scan lasers makes it feasible to locate these lasers at remote locations from each other, the system controller, and/or the experiment. A Hewlett Packard GPIB Bus Extender system has been successfully utilized to solve problems associated with specified limits on the length of the GPIB bus cables. The extender allows the total length of the bus to be increased from 20 meters to up to 1 kilometer. The presence and location of the HP Bus Extender is transparent to the software. Therefore, the extender's insertion in the bus configuration may be customized to best serve the actual application.

GPIB numerical and mnenomic address assignments are listed in FIG. 13. Address changes are not required for equipment items which are moved to or from extended portions of the bus.

It is assumed that the operator is familiar with the standard system commands of the IBM PCDOS operating system including file manipulation, how to run Basic programs, printing of screens and data files, etc. Commercially available IBM PC manuals are the best references for this information.

H. Software

The system software is contained on the system disk which is mounted on the A disk drive. Data files are written to the data disk which is mounted on the B disk drive. FIG. 14 contains a listing of the 10 A disk files which are required to operate the compiled Basic version of the program. COMMAND is the PCDOS system file. ANSI, PRINT, GRAPHICS, and AST-CLOCK are handlers for the screen, printer, graphics and system clock, respectively. CONFIG is the system configuration file. AUTOEXEC is the boot file. KEY makes soft-key assignments which simplify program operation. GPIB is required by the National Instruments GPIB interface board.

The system controller compiled Basic program name is ISCAN. ISCAN contains five primary sections: the main menu, the log file, the rough scan, the high resolution scan and the spectrum analyzer scan. These five sections generate four types of data files, the log file, rough scan date file, high resolution scan data file and spectrum analyzer data file. Three secondary sections of the program allow generation of a data disk directory, reset of selected instruments on the GPIB bus to set up equipment properly for data acquisition, and optimization of system time delays for fastest scanning.

Now that the general operating details of the heterodyne laser spectroscopy system have been described, specific applications of the present invention will next be described in detail.

As previously described, laser heterodyning techniques are, in general, known in the prior art. Laser heterodyning is the mixing of two (or more) laser beams, where each beam has a different predetermined frequency (e.g., $f_1$, $f_2$) A heterodyning action provides a difference frequency component ($f_1$, $f_2$) (as well as a sum frequency) of the laser frequency components.

The difference frequency, if it is within a frequency response range of a suitable detector, can be processed for many applications. The laser heterodyning principle is illustrated in FIG. 15, where a first laser 110 provides an output $P_1$ at a frequency $f_1$.

Similarly, a second laser 112 provides an output $P_2$ at a frequency $f_2$. The output of lasers 110, 112 are imaged through a suitable lens 114 into square law detector 116, the output 117 of which is a signal $i_{det}$, where $$i_{det} = R(P_1 + P_2 + 2\sqrt{P_1 P_2} \cos(2\pi(f_1 - f_2)t + \phi))$$

where
R = detector responsivity (Amperes/Watt)
$P_1$ = optical power of laser 1 (Watts)
$P_2$ = optical power of laser 2 (Watts)
$f_1$ = laser 1 frequency (Hertz)
$f_2$ = laser 2 frequency (Hertz)
$\phi$ = phase angle (radians)

In FIG. 15, the square law detector 116 provides a usable output $i_{det}$. The optical wave fronts of lasers 110, 112 must be perfectly matched. In addition, the spot size of optics 114 must be less than the detector area 116. The focal planes of each laser must be matched to the surface of detector 116.

The difference frequency ($f_1 - f_2$) must be within the frequency response of detector 116 and, finally, polarization of the light signals must be identical.

The laser heterodyning approach illustrated in FIG. 15 is known in the prior art, but is provided for description purposes.

One aspect of the present invention utilizes digital phase locked loop control techniques with laser heterodyning principles to provide a measurement and/or control capability which is believed to be significantly improved over that of prior art techniques.

An example of where laser heterodyning techniques will be utilized is in an atomic vapor laser isotope separation (AVLIS) process. In an AVLIS process, a laser beam of a predetermined frequency is utilized to photoionize an atomic vapor, such as uranium vapor. It is desired to separate the uranium isotopes, particularly $U^{235}$, from the other uranium isotopes. In order to achieve this photoionization capability, it is highly critical that the laser beam used for photoionization purposes be of a specific frequency (wavelength) so that the photoionized $U^{235}$ isotope can be separated from other isotopes, such as $U^{238}$.

It is therefore necessary that the laser beam be of a very specific wavelength to provide this photoionization capability for one particular uranium isotope. The laser heterodyning/digital phase locked loop control technique described herein provides such a capability.

Referring now to FIG. 16, a block diagram of a laser heterodyning/digital phase locked loop control application is depicted. In FIG. 16, the system includes a tunable laser 122, which provides an output light beam having a single, although adjustable, frequency. The tunable laser could provide, for example, an output frequency suitable for use with photoionization of a $U^{235}$ isotope. The output of tunable laser 122 could also be utilized for, if necessary, photoionizing other uranium isotopes. A requirement of tunable laser 122 is, of course, that its output, once adjusted to a predetermined frequency, be extremely stable for photoionization purposes.

In FIG. 16, a second reference laser 120 provides a stable output frequency $f_{ref}$. The outputs of tunable laser 122 and reference laser 120 are optically coupled to detector 124, which provides the laser heterodyning technique described in conjunction with FIG. 16. The difference frequency ($f_1 - f_{ref}$) of detector 124 must be within a predetermined frequency range (e.g., the microwave region), as previously described. The difference frequency from detector 124 is input to a fractional divider circuit (N.n) 126.

Fractional frequency divider circuit 126 provides resolution within 1 Hz increments. The output of divider circuit 126 is input to phase detector 128, together with a 1 MHz signal from oscillator circuit 130.

Oscillator circuit 130 is a highly stable reference signal, which has five parts in $10^{10}$ stability, to provide an accuracy which is necessary for this specific application.

Phase detector 128 provides an output signal (or error signal) which is input to integrator/filter circuit 32 for coupling back to tunable laser circuit 122.

If the output of tunable laser 122 deviates from the desired operating frequency, detector circuit 124 and divider circuit 126 will generate an output signal which correspondingly deviates from that desired signal. Phase detector 128 then generates an error signal, the polarity and magnitude of which will be dependent upon how much and in which direction of polarity the deviation from the desired operating frequency is.

For example, if tunable laser 122 of FIG. 16 has an operating frequency which deviates above the desired frequency, an error signal will be generated which will control tunable laser 122 such that the operating frequency will return to the desired frequency. It can be seen, therefore, that a phase locked loop application, with digital control techniques, can provide a tunable laser which has an output frequency which can be adjustable and which is as stable as the reference frequency of laser 120. Divider 126 can be implemented with a simple keyboard control technique so that an operator need only "key" in the desired operating frequency. The laser heterodyning/digital phase locked loop control technique described herein provides a tunable laser operating frequency which is highly stable for AVLIS purposes.

The phase lock concepts of the present invention are used to lock lasers to identical frequencies. The addition of the digital frequency divider, external reference (1 MHz) oscillator, and the rf phase detector allow the digital selection of an accurate offset frequency between two lasers. The controlled laser's frequency may now be set at any value near that of a reference laser and will remain as stable or accurate as the frequency of the reference laser. The ability of varying the controlled laser's offset frequency is a requirement of applications in LIS spectroscopy, vapor diagnostics, process laser precise frequency offset from a reference, etc.

As previously indicated, another application of laser heterodyne techniques would be a spectroscopy application in an atomic vapor laser isotope separation (AVLIS) process. In an AVLIS process, one critical requirement is determining the spectral isotope components of the atomic vapor, including the uranium 235 isotope. The present invention provides for such a capability by utilizing laser heterodyne techniques with spectroscopy capabilities in the following fashion.

In FIG. 16, if tunable laser 122 has an operating frequency which deviates above the desired frequency, an error signal will be generated which will control tunable laser 122 such that the operating frequency will return to the desired frequency. It can be seen, therefore, that a phase locked loop application, with digital control techniques, can provide a tunable laser which has an output frequency which can be adjustable for sweeping purposes.

The laser system having the sweepable frequency range can then be used in an AVLIS facility wherein the tunable frequency range having been input through an atomic vapor can be combined with the first reference laser with known heterodyne techniques. The heterodyned laser beams can be processed with known spectrum analyzer techniques in order to provide an accurate spectral analysis of the atomic vapor.

Divider 126 of FIG. 16 can be implemented with a simple keyboard control technique so that an operator need only "key" in the desired operating frequency.

The laser heterodyning/digital phase locked loop control technique described herein provides a tunable laser operating frequency which is highly stable for AVLIS purposes.

A further specific application of laser heterodyne techniques is with a spectrum analyzer and pulse counter to measure and/or control pulsed or CW laser frequencies. By varying the "count" of divider 126, a range of tunable frequencies can be achieved subject to the limitations of the tunable laser. By providing a pulsed counter approach, in conjunction with spectrum analyzer techniques at microwave frequencies, it is apparent that the present invention could be utilized to accurately measure and/or control pulsed or CW laser frequencies.

Another application of laser heterodyne techniques according to the present invention is what can be characterized as optical computing, in which an extremely wideband electronic signal generator is provided. The generator provides an output signal deliverable to any destination over a single allband EMI insensitive transmission line such as an optical fiber. The bandwidth of the signal generator can be from DC to the optical frequencies.

As previously described, if tunable laser 122 of FIG. 16 has an operating frequency which deviates above the desired frequency, an error signal will be generated which will control tunable laser 122 such that the operating frequency will return to the desired frequency. It can be seen, therefore, that a phase locked loop application, with digital control techniques, can provide a tunable laser which has an output frequency which can be adjustable and which is as stable as the reference frequency of laser 120. Divider 126 can be implemented with a simple keyboard control technique so that an operator need only "key" in the desired operating frequency.

Since this offset can be adjusted in any suitable manner, it follows that the offset can be adjusted to any predetermined offset within virtually the entire bandwidth between DC and optical frequencies. What is required is a laser heterodyne signal controlled with digital phase locked loop techniques to provide a stable output frequency. This same frequency can be adjusted over a wide range with high precision, as illustrated in FIG. 16.

By providing a plurality of tunable lasers, it would be possible to multiplex different offset frequencies to have a communication capability over a wide bandwidth, yet using a single transmission media.

The present invention generates a microwave signal as the heterodyne difference between two laser signals which may both be transmitted to a destination over the same transmission media, e.g., an optical fiber. Unlike the optical amplitude modulation methods using tunable lasers allows an extremely wide bandwidth for the transmitted signal. A large heterodyne difference (or sum), frequency between two lasers may even be used to generate visible light. Current means of signal generation use many sources to cover different portions of the rf, microwave, infrared and visible spectrum. In essence, a fixed laser and a tunable laser can provide signal generation capability over the entire spectrum from a single source, replacing multiple comparatively narrow bandwidth sources. The advantages of this technique also include electromagnetic interference insensitivity and greatly reduced attenuation for the transmitted signal.

It should be noted that a suitable square law detecting device or detecting nonlinear media is necessary at the receiver. The difference signal is only generated as a result of nonlinear effects.

The present invention provides wideband generation of these signals as a signal source of general utility rather than for a specific end, such as a demodulated, relatively narrow bandwidth communication signal. Although not in use at present, laser heterodyning is the easiest and most practical method to generate and transmit significant signal power in many portions of the spectra, including millimeter waves and the far infrared. The present invention combines the heterodyne and digital phase locked loop concepts to also make frequency stability and accuracy in the laser difference signal possible.

Figure 17:
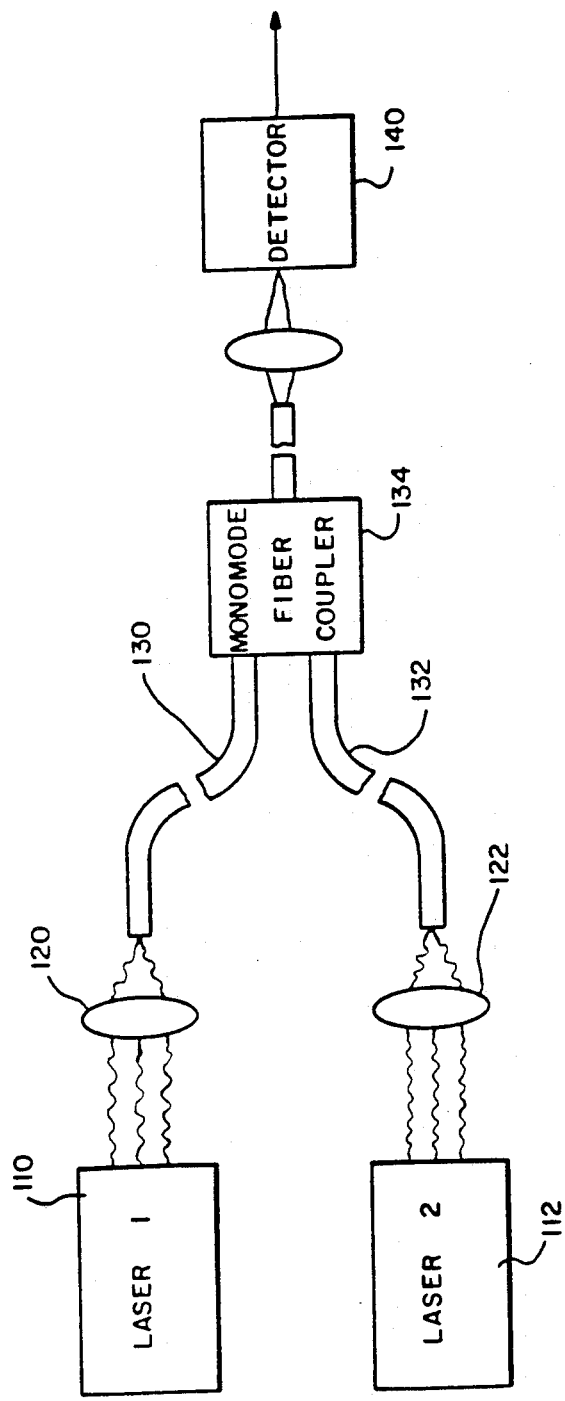
FIG. 17 depicts a block diagram of laser heterodyning by mixing on a monomode fiber according to the present invention.

A further aspect of laser heterodyning with monomode fiber techniques is that there is no requirement that the respective lasers 110, 112 of FIG. 17 be located within the same building. For instance, laser 110 could be located in a first building, laser 112 could be located in a second different building, and the coupler 134 and detector 140 could be located in a third different building. With monomode fiber techniques, the attenuation factor of the laser beams is not so significant as to detract from placing the respective lasers, coupler and detector in different buildings. Even with such a situation, the desired heterodyning frequency range can be achieved without significant attenuation losses. The same efficiency is provided even with the lasers and detector being remotely located from one another. Also, the use of a single mode fiber coupler further reduces alignment complexity by allowing an independent fiber input for each laser signal. These are further aspects of laser heterodyning with monomode fiber techniques.

According to still another aspect of the present invention, it has been observed that use of monomode fibers (typically of four micron core diameter for use with red light) and monomode fiber couplers with laser heterodyne techniques can greatly facilitate further processing. This is because the monomode fiber forces alignment of the laser beams $f_1$, $f_2$ to be mixed or heterodyned, thereby providing improved efficiency. The lasers appear in the fiber as identical point sources due to the four micron diameter of that monomode fiber. This further facilitates transport between different buildings.

Figure 18:
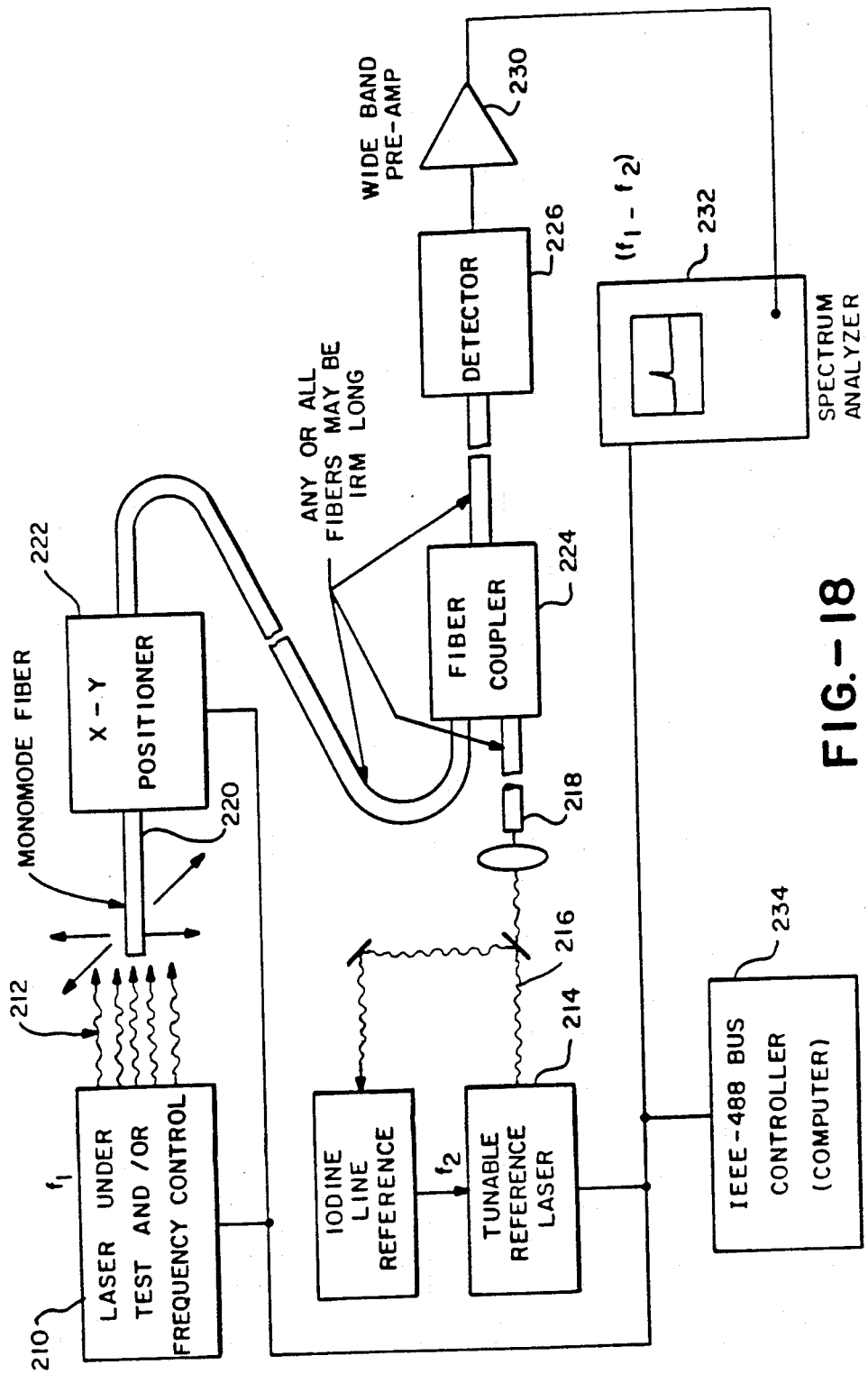
FIG. 18 depicts a block diagram of a laser heterodyne spectra measurement control system according to the present invention.

A further aspect of monomode fibers is the use of monomode fibers with quick disconnect interchangeable connectors, which simplifies measurements on multiple laser sources. In FIG. 18, a laser under test and/or frequency control is illustrated as laser 210. The output of laser 210 is a laser beam 212 which has a frequency spectrum which is desired to be analyzed. It has been found that use of the monomode fiber 220 having a core diameter of four microns can be positioned at any point within the laser beam 212 by an XY positioner circuit 222. The output of the XY positioner 222 is coupled through fiber coupler 224 to detector 226. A reference laser 214 provides a reference laser beam 216 which is input to monomode fiber 218 and to coupler 224. The detector 226 provides a difference frequency output to wideband preamp 230 to spectrum analyzer 232.

Spectrum analyzer 232 provides the necessary spectral analysis processing capability so that spectral analysis of laser beam 212 can be achieved by the positioning of monomode fiber 220 at any predetermined point of laser beam 212. This aspect of laser heterodyning with monomode fibers provides a further desired capability.

Still another aspect of the present invention relates to spectral analysis of spurious emissions and modes in laser heterodyne applications. One apparent problem with laser systems is the analysis of optical frequencies having spurious emissions and modes. Prior art systems are not in general capable of spectral processing at the optical frequencies. By utilizing a laser heterodyne/homodyne technique with spectral analysis, it is possible, as will be described below, to provide suitable processing techniques for the detection of spurious emissions and modes.

With a homodyne technique, such as illustrated in FIGS. 19-20, any spurious emissions tend to "beat" against one another, resulting in a transformed signal such as shown in FIG. 20. By utilizing a heterodyne/homodyne application with spectral analysis, as illustrated in FIGS. 19-20, the present invention can provide improved control capabilities for spurious emissions and modes. This provides further control of the laser spectrum which is highly desirable, particularly in an AVLIS (atomic vapor laser isotope separation) process.

What is claimed is:

1. In an atomic vapor laser isotope separation process, a laser spectroscopy system comprising
   a first reference laser for generating a first laser beam having a first reference laser frequency,
   a second tunable laser for generating as an output a plurality of second laser beams having a range of laser frequencies,
   means for sweeping said second laser to generate said second laser beams including phase locked loop control means for adjusting said output of said second laser to predetermined frequency outputs, said control means including means for varying the frequency of said second laser,
   means for coupling said second laser beams into an atomic vapor having spectral isotope components,
   means for heterodyning said first referenced laser frequency and frequencies of said second laser beam to form heterodyned frequencies, and
   means for processing said heterodyned frequencies to determine said spectral components of said atomic vapor.

* * * * *